(12) United States Patent
Muraki

(10) Patent No.: US 8,350,231 B2
(45) Date of Patent: Jan. 8, 2013

(54) OPTICAL MEASUREMENT APPARATUS, FLOW SITE METER AND OPTICAL MEASUREMENT METHOD

(75) Inventor: Yosuke Muraki, Tokyo (JP)

(73) Assignee: Sony Corporation, Tokyo (JP)

( * ) Notice: Subject to any disclaimer, the term of this patent is extended or adjusted under 35 U.S.C. 154(b) by 401 days.

(21) Appl. No.: 12/792,271

(22) Filed: Jun. 2, 2010

(65) Prior Publication Data

US 2010/0314555 A1 Dec. 16, 2010

(30) Foreign Application Priority Data

Jun. 11, 2009 (JP) ................................. P2009-140043

(51) Int. Cl.
*G01J 1/58* (2006.01)
*G01T 1/10* (2006.01)
*H01J 65/06* (2006.01)
*H01J 65/08* (2006.01)

(52) U.S. Cl. .................. 250/459.1; 250/461.2

(58) Field of Classification Search ............... 250/459.1, 250/461.2
See application file for complete search history.

(56) References Cited

U.S. PATENT DOCUMENTS

| | | | | |
|---|---|---|---|---|
| 4,573,796 A | * | 3/1986 | Martin et al. ................ | 356/318 |
| RE35,868 E | * | 8/1998 | Kosaka ........................ | 250/574 |
| 5,827,660 A | * | 10/1998 | Singer et al. ................. | 435/6.11 |
| 6,897,954 B2 | * | 5/2005 | Bishop et al. ................ | 356/317 |
| 7,605,388 B2 | * | 10/2009 | Carter et al. ................. | 250/573 |
| 7,782,512 B2 | * | 8/2010 | Shinoda ..................... | 359/196.1 |
| 7,945,428 B2 | * | 5/2011 | Fox et al. ..................... | 702/189 |
| 8,171,777 B2 | * | 5/2012 | Schilffarth .................. | 73/61.71 |
| 2006/0219873 A1 | * | 10/2006 | Martin et al. ............. | 250/214 R |
| 2009/0057569 A1 | | 3/2009 | Shinoda | |

FOREIGN PATENT DOCUMENTS

| | | |
|---|---|---|
| JP | 2005US001866 | 7/2005 |
| JP | 2007-518991 | 6/2007 |
| JP | 2009-063305 | 3/2009 |
| JP | 2007-101314 | 4/2010 |

\* cited by examiner

*Primary Examiner* — David Porta
*Assistant Examiner* — Edwin Gunberg
(74) *Attorney, Agent, or Firm* — K&L Gates LLP

(57) ABSTRACT

Disclosed herein is an optical measurement apparatus including at least: a flow channel through which samples flow; a first light radiation section; a first opto-electrical conversion section; a first analog-to-digital conversion section; a second light radiation section; a second light detection section; a second opto-electrical conversion section; an amplification section; and a second analog-to-digital conversion section.

10 Claims, 8 Drawing Sheets

OPTICAL MEASUREMENT APPARATUS, FLOW SITE METER AND OPTICAL MEASUREMENT METHOD

CROSS REFERENCES TO RELATED APPLICATIONS

The present application claims priority to Japanese Priority Patent Application JP 2009-140043 filed in the Japan Patent Office on Jun. 11, 2009, the entire content of which is hereby incorporated by reference.

BACKGROUND

The present application relates to an optical measurement apparatus for optically detecting a sample by a flow channel. To put it in detail, the present application relates to an optical measurement apparatus for optically detecting a sample flowing through a flow channel, a flow site meter making use of the optical measurement apparatus and an optical measurement method adopted by the optical measurement apparatus.

In recent years, with progress of an analysis technique, there is also developed a technique for measuring microparticles, analyzing the measured microparticles and sorting the analyzed microparticles in a process of driving the microparticles to flow through a flow channel. In the process for which the technique is developed, biological microparticles or general microparticles are driven to flow through a flow channel. Typical examples of the biological microparticle are a cell and a microorganism whereas a typical example of the general microparticle is a microbead. A typical example of the technique for measuring microparticles flowing through a flow channel, analyzing the measured microparticles and sorting the analyzed microparticles is an analysis technique referred to as a flow-site-metry technique. The technological improvement of flow-site-metry technique is making progress very fast.

The flow-site-metry technique is an analysis technique in accordance with which microparticles serving as the subject of an analysis are driven into fluid in an aligned state, laser light or the like is radiated to the microparticles in order to detect fluorescent or scattered light emitted by the microparticles due to the radiation and, on the basis of the detected fluorescent or scattered light, the microparticles are measured, analyzed and sorted. A flow-site-metry process is carried out in a total system which can be divided into a fluid system, an optical system, an electrical system and a sorting system. The fluid system, the optical system, the electrical system and the sorting system are described as follows.

(1): Fluid System

In the fluid system, the microparticles serving as the subject of an analysis are aligned on a line inside a flow cell (or a flow channel). To put it more concretely, a sheath flow is driven to enter a flow cell at a fixed flow rate and, in this state, a sample flow including the microparticles is injected slowly into the center of the flow cell. At that time, in accordance with the laminar flow principle, the sheath flow and the sample flow do not mix with each other. Instead, the sheath flow and the sample flow form a laminated flow which is a flow including flow layers. Then, in accordance with, among other quantities, the size of each of the microparticles serving as the subject of an analysis, the flow rates of the sheath flow and the sample flow are adjusted in order to drive each of the microparticles in an aligned state.

(2): Optical System

In the optical system, laser light or the like is radiated to the microparticles serving as the subject of an analysis and fluorescent or scattered light emitted by the microparticles due to the radiation is detected. Each of the microparticles put in an aligned state in the fluid system (1) is driven to flow through a laser radiation section and, every time one of the microparticles passes through the laser radiation section, fluorescent or scattered light emitted by the microparticle due to the radiation of the laser light to the microparticle is detected by an optical detector for every parameter in order to analyze the microparticle.

(3): Electrical System

In the electrical system, optical information detected by the optical system (2) is converted into an analog electrical signal which is a train of voltage pulses. The resulting analog electrical signal is then subjected to an analog-to-digital conversion process. Subsequently, on the basis of digital data obtained as a result of the analog-to-digital conversion process, computer software provided for analyses is used to produce an extracted histogram in an analysis.

(4): Sorting System

In the sorting system, the microparticles completing the measurement processes carried out in the fluid system (1), the optical system (2) and the electrical system (3) are separated from each other before being collected. In accordance with a representative sorting method, plus and minus electrical charges are added to the microparticles completing the measurement processes and the flow cell is sandwiched by two deflection plates D which have electrical potentials different from each other. Each of the electrically charged microparticles is attracted by one of the two deflection plates D in accordance with the polarity of the electrical charge added to the microparticle.

A technology such as the flow-site-metry technology for analyzing and sorting microparticles flowing through a flow channel is widely used in a variety of fields such as the medical field, the pharmaceutical field, the clinical examination field, the food field, the agricultural field, the engineering field, the forensic pathological field and the criminal identification field. Particularly, in the case of the medical field, the flow-site-metry technology plays an important role in subfields such as pathology, tumor immunology, transplantations, genetics, regenerative medicine and chemotherapy.

As described above, the technology for measuring microparticles flowing through a flow channel, for analyzing the measured microparticles and for sorting the analyzed microparticles is required a very wide variety of fields. A flow-site-metry process adopting the flow-site-metry technique based on this technology is carried out in a total system which can be divided into the fluid system, the optical system, the electrical system and the sorting system as described above. The development of the technology required for carrying out processes in the fluid system, the optical system, the electrical system and the sorting system is making progress from day to day. For example, as disclosed in Japanese Patent Laid-Open No. 2007-101314 (hereinafter referred to as Patent Document 1), there has been proposed a microparticle analysis apparatus in which microparticle suspension liquid including dyed microparticles serving as the subject of an analysis is generated and light is radiated to a flow of the microparticle suspension liquid in order to obtain a plurality of optical signals having different types each reflecting the characteristic of a microparticle. Each of the optical signals is then converted into an output electrical signal so that analyses having a variety of types different from each other can be carried out by the microparticle analysis apparatus even without preparing signal processing circuit boards with a plurality of different types.

As disclosed in JP-T-2007-518991, on the other hand, there has been proposed a method for widening the dynamic range of a flow site meter. In accordance with this method, fluorescent light radiated by a single light source is split into a plurality of fluorescent light beams and, by detecting these fluorescent light beams, the dynamic range of a flow site meter can be increased.

JP-T-2009-063305 discloses a method for eliminating radiation irregularities and shifts of the radiation position as well as shifts of the focal position. In accordance with this method, directional light is radiated to a sample in order to obtain information on the position of the sample in a flow channel. Then, on the basis of the information, directional light is radiated again to the sample in order to eliminate radiation irregularities and shifts of the radiation position as well as shifts of the focal position.

SUMMARY

As described above, a variety of technologies has been proposed for each of the processes. Information on samples flowing through a flow channel is analyzed by analyzing results of an AD (analog-to-digital) conversion process carried out on the information. It is thus very important to raise the precision of the results of an AD conversion process. In order to raise the precision of the results of an AD conversion process, it is desirable to increase the input range of the AD conversion process and increase the number of output bits. It is to be noted, however, that the input range of the AD conversion IC itself is fixed whereas the number of output bits for the AD conversion IC is a value in the range 16 to 18.

In addition, in order to make the input range of the AD conversion process adjustable on a real-time basis, there is conceived a method for delaying raw analog data generated by an optical pickup. However, this method raises a problem that an electrical process of delaying the raw analog data adversely deteriorates the data. The electrical process of delaying the raw analog data is also referred to as an analog-data delaying process.

In order to avoid the problems described above, in accordance with the existing technologies, the first several tens to several hundreds of samples are used for adjusting the gain of an amplifier. Thus, if this method is adopted, there is raised a problem that the data of the first several tens to several hundreds of samples is undesirably wasted. In addition, if the samples used for adjusting the gain in advance in accordance with this method are a mixture of microparticles and megacells, optimization is not possible.

As described above, in the technology for optically detecting samples flowing through a flow channel, a technique for improving the precision of the result of an AD (analog-to-digital) conversion process raises a variety of problems described above.

It is therefore desirable to provide a technique adopted in the technology for optically detecting samples flowing through a flow channel to serve as a technique innovated for improving the precision of the result of the AD (analog-to-digital) conversion process with a high degree of efficiency and with a high degree of reliability.

As a result of research conducted earnestly, paying attention to a characteristic phenomenon in which samples are moving through a flow channel, inventors of the present application have developed a method for amplifying an electrical signal generated by a process carried out in the electrical system and have led to completion of the present application.

First of all, the present application provides an optical measurement apparatus employing at least: a flow channel through which samples flow; a first light radiation section configured to radiate light to the samples flowing through the flow channel; a first light detection section configured to detect optical information emitted from the samples due to the light radiated by the first light radiation section; and a first opto-electrical conversion section configured to carry out an opto-electrical conversion process of converting the optical information detected by the first light detection section into an analog electrical signal. The optical measurement apparatus further employs at least: a first AD (analog-to-digital) conversion section configured to carry out an AD conversion process of converting the analog electrical signal, which is output by the first opto-electrical conversion section into a digital electrical signal; a second light radiation section provided on the downstream side of the flow channel with respect to the first light radiation section to serve as a light radiation section configured to radiate light to the samples; and a second light detection section configured to detect optical information emitted from the samples due to the light radiated by the second light radiation section. The optical measurement device further employs at least: a second opto-electrical conversion section configured to carry out an opto-electrical conversion process of converting the optical information detected by the second light detection section into an analog electrical signal; an amplification section configured to amplify the analog electrical signal, which is output by the second opto-electrical conversion section, on the basis of the digital electrical signal output by the first AD conversion section as a result of the AD conversion process; and a second AD conversion section configured to convert the analog electrical signal amplified by the amplification section into a digital electrical signal. In the optical measurement apparatus according to an embodiment, the samples flow through the flow channel. Thus, it is possible to provide second sections on the downstream side of the flow channel with respect to the first sections to improve the accuracy of information obtained by the second sections making use of information obtained by the first sections. It is to be noted that the optical measurement apparatus according to an embodiment is provided with the second sections as well as the first sections, it is, however, possible to control not to operate the second sections depending on the information obtained by the first sections as will be described later.

The optical measurement apparatus according to an embodiment can be well applied to a flow site meter and can serve as an apparatus for implementing an optical measurement method provided by the present application.

To put it more concretely, by providing the optical measurement apparatus according to an embodiment with a sample sorting section configured to sort samples in accordance with the digital electrical signal output by the second AD conversion section, the optical measurement apparatus can be used as the flow site meter.

The technical term "sample" used in the description of the present application is defined as follows. A sample can be any substance as long as the substance is capable of flowing through a flow channel. Typical examples of the sample are a biological microparticle and a synthesis particle. Typical examples of the biological microparticle are a cell, a microorganism, a liposome, a DNA substance and a protein substance whereas typical examples of the synthesis particle are a latex particle, a gel particle and an industrial particle.

In the optical measurement apparatus according to an embodiment, an analog electrical signal generated as the final result of measurement processes carried out by the second sections on samples is amplified at an optimum amplification gain determined on the basis of a digital electrical signal generated as the final result of measurement processes carried out by the first sections on the same samples. The analog electrical signal amplified at the optimum amplification gain is then converted by the second AD conversion section into a digital electrical signal eventually output by the optical measurement apparatus. Thus, without wasting samples, it is possible to efficiently and reliably improve the precision of the digital electrical signal.

Additional features and advantages are described herein, and will be apparent from the following Detailed Description and the figures.

DETAILED DESCRIPTION

The present application is described in detail below with reference to these drawings according to an embodiment.

1: Optical Measurement Apparatus 1
(1-1): Flow channel 2
(1-2): First Light Radiation Section 11
(1-3): First Light Detection Section 12
(1-4): First Opto-Electrical Conversion Section 13
(1-5): First AD Conversion Section 14
(1-6): Second Light Radiation Section 21
(1-7): Second Light Detection Section 22
(1-8): Second Opto-Electrical Conversion Section 23
(1-9): Amplification Section 3
(1-10): Second AD Conversion Section 24
(1-11): Flow-Rate Measurement Section 4
(1-12): Flow-Rate Control Section 5
(1-13): Temperature Control Section 6
2: Flow Site Meter
(2-1): Sorting Section 7
3: Optical Measurement Method
(3-1): Flow Process I
(3-2): First Light Radiation Process II
(3-3): First Light Detection Process III
(3-4): First Opto-Electrical Conversion Process IV
(3-5): First AD Conversion Process V
(3-6): Second Light Radiation Process VI
(3-7): Second Light Detection Process VII
(3-8): Second Opto-electrical conversion process VIII
(3-9): Amplification Process IX
(3-10): Second AD Conversion Process X
(3-11): Flow-Rate Measurement Process XI
(3-12): Flow-Rate Control Process XII
(3-13): Temperature Control Process XIII
(3-14): Sorting Process XIV
1: Optical Measurement Apparatus 1

Figure 1:
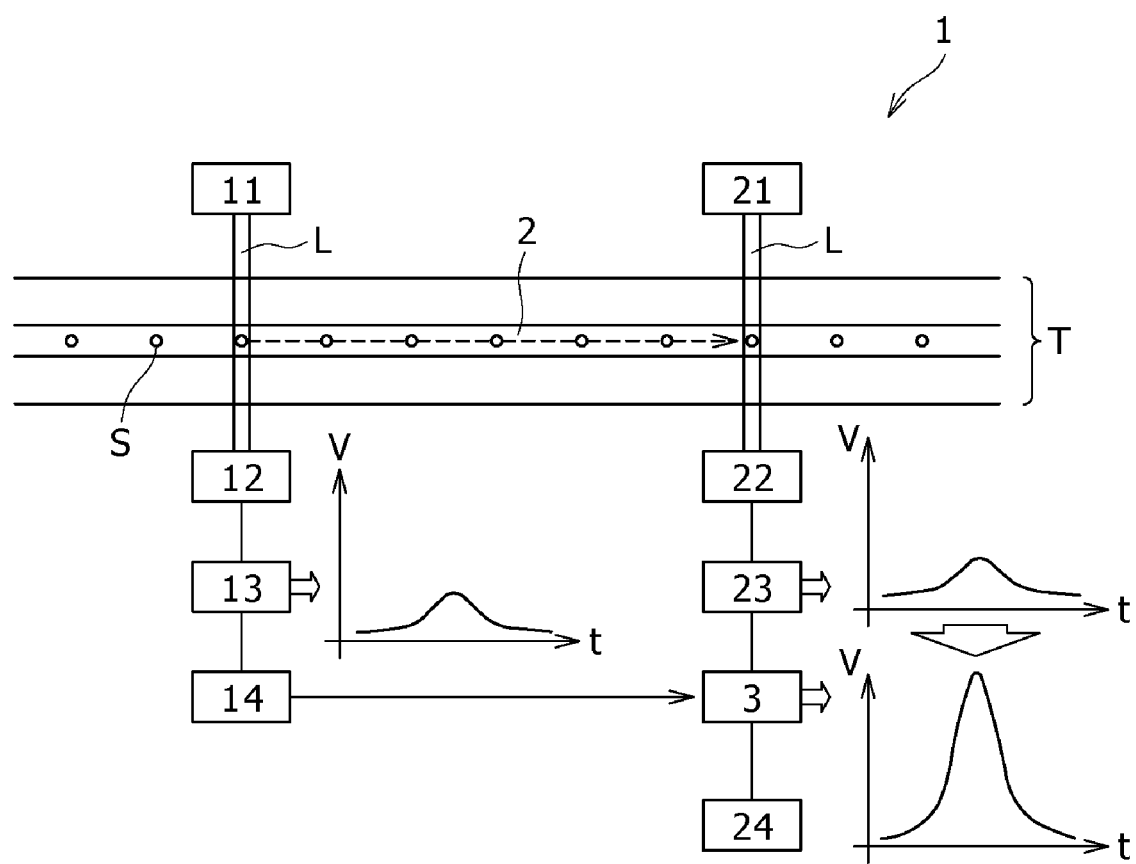
FIG. 1 is a conceptual diagram showing a model of an optical measurement apparatus according to an embodiment.

FIG. 1 is a conceptual diagram showing a model of an optical measurement apparatus 1 according to an embodiment.

As shown in the figure, the optical measurement apparatus 1 according to an embodiment employs a flow channel 2, a first light radiation section 11, a first light detection section 12, a first opto-electrical conversion section 13, a first AD (analog-to-digital) conversion section 14, a second light radiation section 21, a second light detection section 22, a second opto-electrical conversion section 23, an amplification section 3 and a second AD conversion section 24. If necessary, the optical measurement apparatus 1 can be provided with other sections such as a flow-rate measurement section 4, a flow-rate control section 5 and a temperature control section 6. Each of the sections composing the optical measurement apparatus 1 is explained in detail as follows.

(1-1): Flow Channel 2

Samples S are flowing through the flow channel 2. Each of the first light radiation section 11 and the second light radiation section 21 which will be described later radiates light to predetermined members of the samples S in order to detect various kinds of information on the members.

The shape of the flow channel 2 usable in the optical measurement apparatus 1 according to an embodiment is not prescribed in particular. Instead, the shape of the flow channel 2 can be designed with a high degree of freedom. In the case of the optical measurement apparatus 1 shown in FIG. 1 for example, the flow channel 2 is constructed inside a 2-dimensional or 3-dimensional base T which is typically made of a material such as plastic or glass. However, a flow channel having another shape can be used as the flow channel 2. For example, it is possible to provide the optical measurement apparatus 1 with a flow channel 2 employed in the existing flow site meter as is the case with another embodiment shown in FIG. 2.

In addition, each of the width, depth and cross section of the flow channel 2 is also not prescribed in particular either but can be determined with a high degree of freedom. For example, a micro flow channel having a path width not greater than 1 mm can also be used as the flow channel 2 of the optical measurement apparatus 1 according to an embodiment. In particular, by a micro flow channel having a path width in the range 10 micrometers to 1 mm, it is possible to adopt an optical measurement method provided by the present invention as will be described later.

It is to be noted that, if a flow channel 2 constructed on a base T is employed, it is desirable to make the bottom of the flow channel 2 from a transparent material. In the case of the optical measurement apparatus 1 shown in FIG. 1, on the upstream side of the sample flow through the flow channel 2, the base T is flanked by the first light radiation section 11 provided above the base T and the first light detection section 12 provided below the base T. By the same token, on the downstream side of the sample flow through the flow channel 2, the base T is flanked by the second light radiation section 21 provided above the base T and the second light detection section 22 provided below the base T. In such a configuration, it is thus possible to detect optical information generated through the transparent bottom of the flow channel 2.

(1-2): First Light Radiation Section 11

The first light radiation section 11 is a section for radiating light L to samples S which are flowing through the flow channel 2.

The type of the light L radiated by the first light radiation section 11 is not prescribed in particular. It is desirable, however, to radiate light L having a constant direction, a constant wavelength and a constant intensity in order to obtain fluorescent or scattered light, which is generated by the samples S, with a high degree of reliability. For example, the light L radiated by the first light radiation section 11 is laser light or light emitted by an LED (Light Emitting Device). If laser light is radiated by the first light radiation section 11 as the light L, the type of the laser light is also not prescribed in particular either. That is to say, the type of the laser can be any laser type or a combination of laser types. Typical examples of the laser type are an Ar (argon ion) laser, an He—Ne (helium-neon) laser, a dye laser and a Kr (Krypton) laser.

(1-3): First Light Detection Section 12

The first light detection section 12 is a section for detecting optical information which is generated by the samples S due to radiation of light L from the first light radiation section 11 to the samples S.

The type of the first light detection section 12 usable in the optical measurement apparatus 1 according to an embodiment is not prescribed in particular. That is to say, the type of first light detection section 12 can be any type as far as the first light detection section 12 is capable of detecting the optical information generated by the samples S. In other words, the first light detection section 12 to be employed in the optical measurement apparatus 1 can be selected among commonly known light detectors with a high degree of freedom. As an alternative, the first light detection section 12 can be constructed by combining two or more commonly known light detectors having different types with a high degree of freedom. Typical examples of the commonly known light detectors are a fluorescent-light measurement device, a scattered-light measurement device, a transmitted-light measurement device, a reflected-light measurement device, a diffracted-light measurement device, an ultraviolet-light spectral measurement device, an infrared-light spectral measurement device, a Raman spectral measurement device, a FRET measurement device, a FISH measurement device, other spectroscopes of a variety of types and the so-called multi-channel light detector which is an array including a plurality of light detectors.

Figure 2:
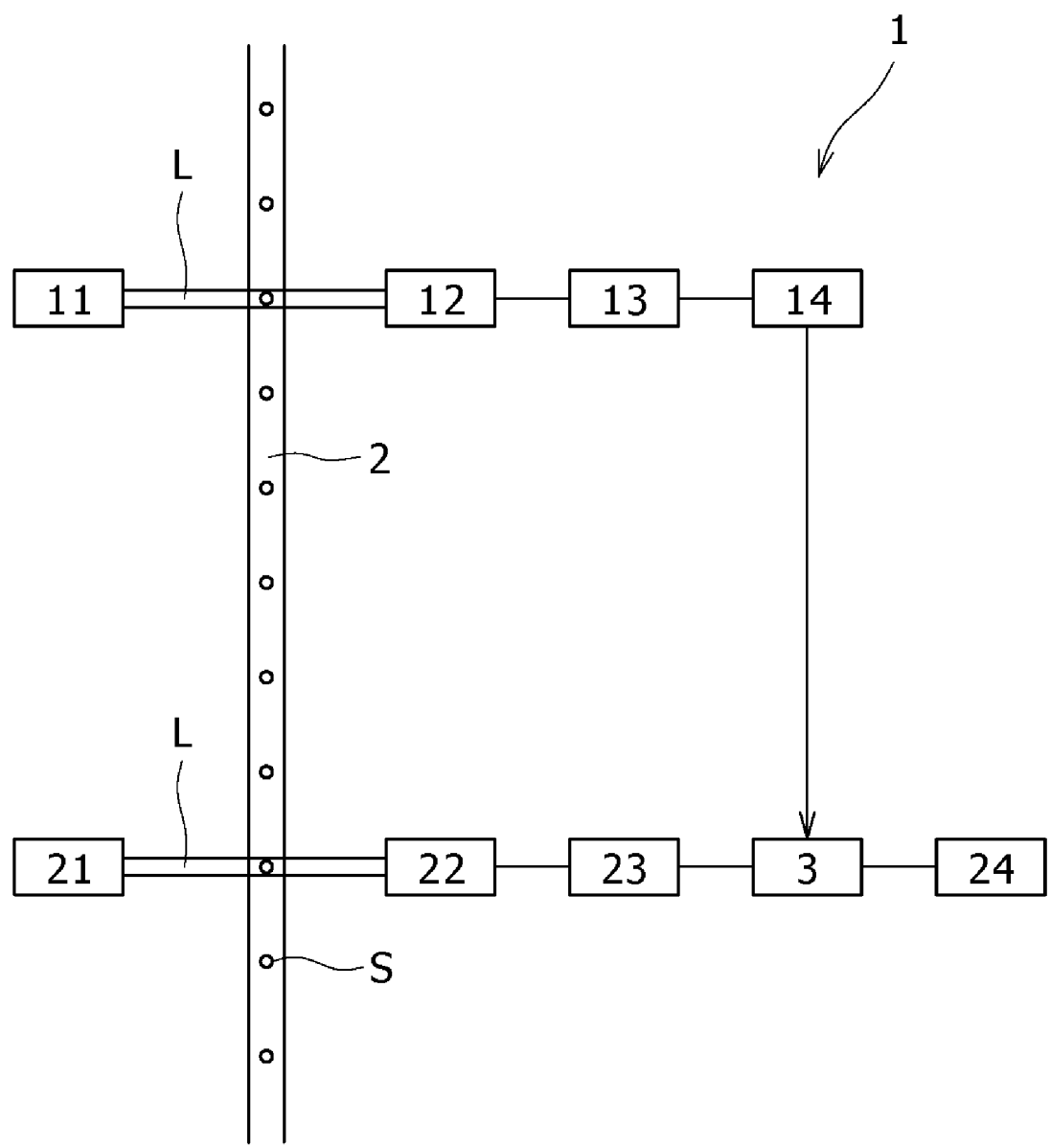
FIG. 2 is a conceptual diagram showing a model of an optical measurement apparatus according to another embodiment which is different from the embodiment shown in FIG. 1.

In addition, the position at which the first light detection section 12 is installed in the optical measurement apparatus 1 is also not prescribed in particular either. That is to say, the first light detection section 12 can be installed at any position in the optical measurement apparatus 1 as long as, at the position, the first light detection section 12 is capable of detecting optical information generated by the samples S. Thus, the position at which the first light detection section 12 is installed in the optical measurement apparatus 1 can be selected and designed with a high degree of freedom. For example, the first light detection section 12 is installed in the optical measurement apparatus 1 at a position on a side opposite to the first light radiation section 11 with respect to the flow channel 2 as shown in FIGS. 1 and 2. By installing the first light detection section 12 in the optical measurement apparatus 1 at a position on a side opposite to the first light radiation section 11 with respect to the flow channel 2, the first light radiation section 11 and the second light radiation section 21 to be described later can be placed in a freer configuration.

(1-4): First Opto-Electrical Conversion Section 13

The first opto-electrical conversion section 13 is a section for converting the optical information detected by the first light detection section 12 into an analog electrical signal. The analog electrical signal generated by the first opto-electrical conversion section 13 is typically a voltage pulse. In FIG. 1, the voltage pulse is pointed to by an arrow→which is appended to the right side of the first opto-electrical conversion section 13.

(1-5): First AD Conversion Section 14

The first AD conversion section 14 is a section for carrying out an AD (analog-to-digital) conversion process to convert an analog electrical signal output by the first opto-electrical conversion section 13 into a digital electrical signal.

In the existing optical measurement apparatus, the AD conversion process to convert a voltage pulse serving as an analog electrical signal into a digital electrical signal is normally carried out after amplifying the analog electrical signal at a gain which is determined in advance. In the case of the optical measurement apparatus 1 according to an embodiment, however, it is not necessary to set the gain in advance. That is to say, the first AD conversion section 14 carries out the first AD conversion process after amplifying the analog electrical signal at any arbitrary gain. It is needless to say that the first AD conversion section 14 may also carry out the first AD conversion process to convert a voltage pulse serving as an analog electrical signal into a digital electrical signal without amplifying the analog electrical signal.

The digital electrical signal obtained as a result of the AD conversion process carried out by the first AD conversion section 14 is used for determining the gain of the amplification section 3 to be described later.

(1-6): Second Light Radiation Section 21

The second light radiation section 21 is a section provided on the downstream side of the flow channel 2 with respect to the first light radiation section 11 to serve as a section for radiating light to the samples S. That is to say, the second light radiation section 21 is also capable of again radiating light L to the same samples S to which light has been radiated by the first light radiation section 11. In most of the existing optical measurement apparatus each making use of a flow channel, the optical measurement of samples S flowing through the flow channel is generally carried out only once. In the case of the optical measurement apparatus 1 according to an embodiment, however, the optical measurement of the samples S can be carried out as many times as needed, provided that the samples S are flowing through the flow channel 2. Thus, in the optical measurement apparatus 1 according to an embodiment, the second light radiation section 21 is provided to serve as a section which is capable of re-radiating light to the samples S after radiation of light from the first light radiation section 11 to the samples S while the samples S are flowing through the flow channel 2.

It addition, in accordance with results produced in a variety of measurement processes carried out by the first light detection section 12, the first opto-electrical conversion section 13 and the first AD conversion section 14, it is free to select an option not to operate the second light radiation section 21. For example, if the results produced in a variety of measurement processes carried out by the first light detection section 12, the first opto-electrical conversion section 13 and the first AD conversion section 14 are already ideal data, there is a conceivable case in which it is not necessary to carry out measurement processes with a high degree of precision by the second light radiation section 21, the second light detection section 22, the second opto-electrical conversion section 23, the amplification section 3 and the second AD conversion section 24.

In a case in which two or more samples S are flowing continuously or in similar cases, even if measurement processes are carried out by the second light radiation section 21, the second light detection section 22, the second opto-electrical conversion section 23, the amplification section 3 and the second AD conversion section 24, it is not possible to obtain data which can be used for analyzing the samples S.

Figure 3:
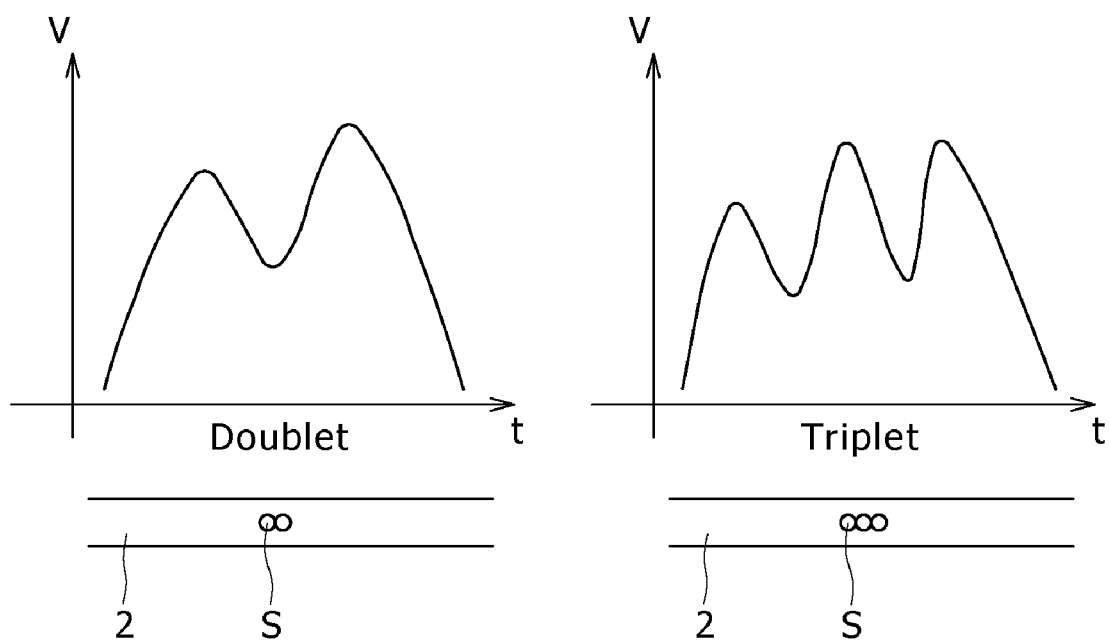
FIG. 3 is a diagram showing graphs representing a pulse signal of two contiguous samples flowing in the form of a doublet and a pulse signal of three contiguous samples flowing in the form of a triplet.

FIG. 3 is a diagram showing graphs representing a pulse signal of two contiguous samples S flowing in the form of a doublet and a pulse signal of three contiguous samples S flowing in the form of a triplet. Each of the pulse signal of the two contiguous samples S flowing in the form represented by the doublet graph shown in FIG. 3 and the pulse signal of the three contiguous samples S flowing in the form represented by the triplet graph shown in FIG. 3 undesirably has a plurality of peaks so that the samples S cannot be analyzed. If such results are eventually produced in measurement processes carried out by the first light detection section 12, the first opto-electrical conversion section 13 and the first AD conversion section 14, control can be executed to select an option not to operate the second light radiation section 21. Thus, wasteful measurement processes can be eliminated. As a result, necessary measurement processes can be carried out with a high degree of efficiency. In addition, since unanalyzable data can be omitted in advance, it is possible to simplify an algorithm which is required for analyzing data obtained as a result of the necessary measurement processes.

By the same token, the type of the light L radiated by the second light radiation section 21 is also not prescribed in particular either. It is desirable, however, to radiate light L having a constant direction, a constant wavelength and a constant intensity in order to obtain fluorescent or scattered light, which is generated by the samples S, with a high degree of reliability. For example, the light L radiated by the second light radiation section 21 is laser light or light emitted by an LED (Light Emitting Device). If laser light is radiated by the second light radiation section 21 as the light L, the type of the laser light is also not prescribed in particular either. That is to say, the type of the laser can be any laser type or a combination of laser types. Typical examples of the laser type are an Ar (argon ion) laser, an He—Ne (helium-neon) laser, a dye laser and a Kr (Krypton) laser.

Figure 4:
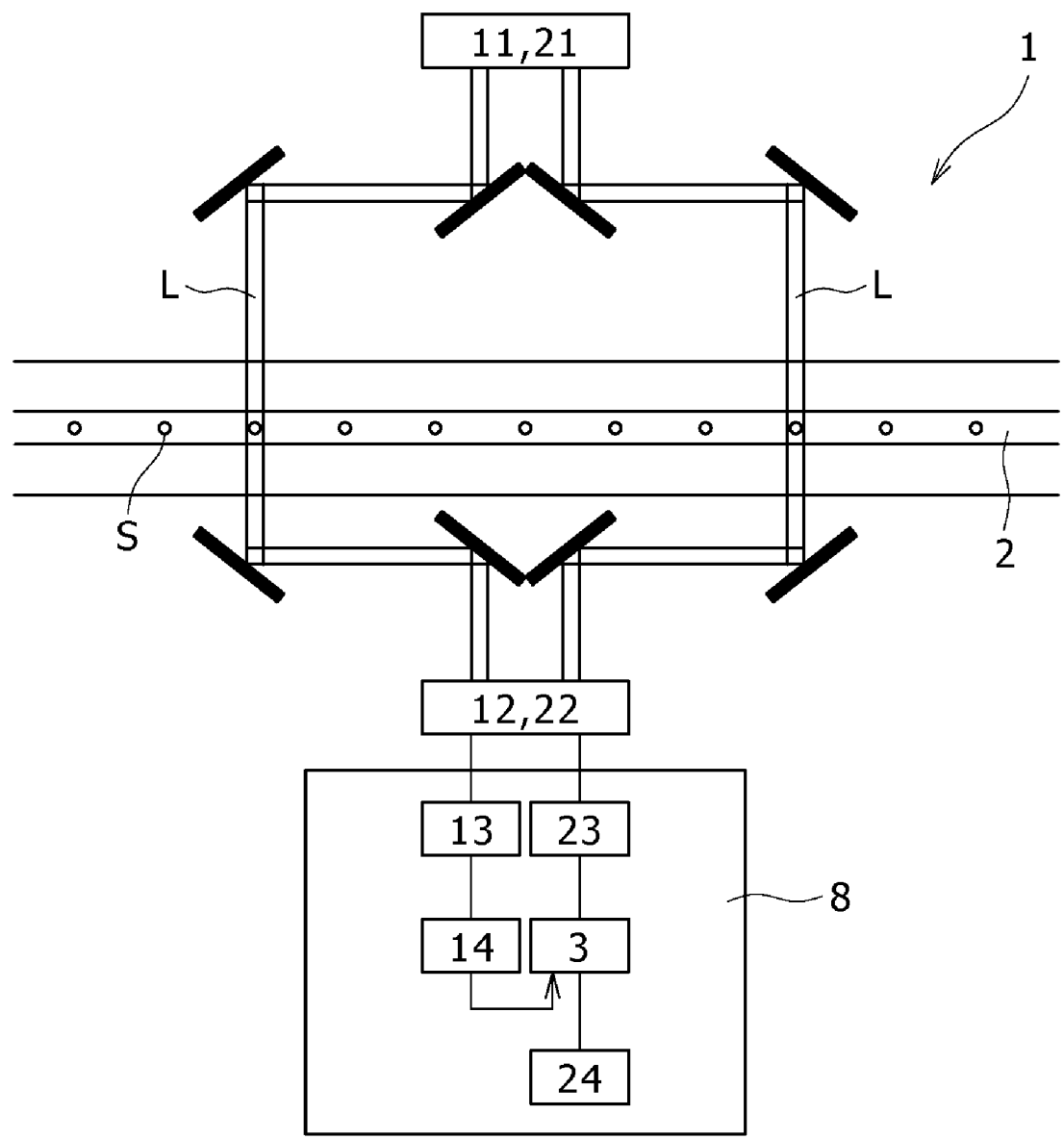
FIG. 4 is a conceptual diagram showing a model of an optical measurement apparatus according to a further embodiment which is different from the embodiments shown in FIGS. 1 and 2.

The second light radiation section 21 can be provided as a section separated from the first light radiation section 11 or integrated with the first light radiation section 11 as shown in FIG. 4. FIG. 4 is a conceptual diagram showing a model of an optical measurement apparatus 1 according to a further embodiment which is different from the embodiments shown in FIGS. 1 and 2. As shown in FIG. 4, the optical path of light L radiated by the first light radiation section 11 is split into two beams. That is to say, the first light radiation section 11 appears to also function as the second light radiation section 21. By integrating the second light radiation section 21 with the first light radiation section 11 to form a single light source in the optical measurement apparatus 1 in this way, the single light source can contribute to the downsizing of the optical measurement apparatus 1.

(1-7): Second Light Detection Section 22

The second light detection section 22 is a section for detecting optical information which is generated by the samples S due to radiation of light from the second light radiation section 21 to the samples S. In the optical measurement apparatus 1 according to an embodiment, the second light detection section 22 serves as a section for again detecting optical information generated by the samples S, optical information generated by which has already been detected by the first light detection section 12, while the samples S are flowing through the flow channel 2.

It is to be noted that, if an option to deactivate the second light radiation section 21 is selected on the basis of the results produced in the measurement processes carried out by the first sections 12, 13 and 14, control can also be executed so as not to operate the second light detection section 22.

The type of the second light detection section 22 usable in the optical measurement apparatus 1 according to an embodiment is not prescribed in particular. That is to say, the type of the second light detection section 22 can be any type as far as the second light detection section 22 is capable of detecting the optical information generated by the samples S. In other words, the second light detection section 22 to be employed in the optical measurement apparatus 1 can be selected among commonly known light detectors with a high degree of freedom. As an alternative, the second light detection section 22 can be constructed by combining two or more commonly known light detectors having different types with a high degree of freedom. Typical examples of the commonly known light detectors are a fluorescent-light measurement device, a scattered-light measurement device, a transmitted-light measurement device, a reflected-light measurement device, a diffracted-light measurement device, an ultraviolet-light spectral measurement device, an infrared-light spectral measurement device, a Raman spectral measurement device, a FRET measurement device, a FISH measurement device, other spectroscopes of a variety of types and the so-called multi-channel light detector which is an array of a plurality of light detectors.

In addition, the position at which the second light detection section 22 is installed in the optical measurement apparatus 1 is not prescribed in particular. That is to say, the second light detection section 22 can be installed at any position in the optical measurement apparatus 1 as long as, at the position, the second light detection section 22 is capable of detecting optical information generated by the samples S. Thus, the position at which the second light detection section 22 is installed in the optical measurement apparatus 1 can be selected and designed with a high degree of freedom. For example, the second light detection section 22 is installed in the optical measurement apparatus 1 at a position on a side opposite to the second light radiation section 21 with respect to the flow channel 2 as shown in FIGS. 1 and 2. By installing the second light detection section 22 in the optical measurement apparatus 1 at a position on a side opposite to the second light radiation section 21 with respect to the flow channel 2 in this way, the second light radiation section 21 and the first light radiation section 11 described earlier can be placed in a freer configuration.

The second light detection section 22 can be provided as a section separated from the first light detection section 12 or integrated with the first light detection section 12 as shown in FIG. 4. As shown in FIG. 4, the first light detection section 12 is driven to appear to also function as the second light detection section 22. With the first light detection section 12 driven to appear to also function as the second light detection section 22, in order to prevent optical information from being detected out off a sample S receiving light L radiated by the first light radiation section 11 while flowing through the flow channel 2 at the same time as optical information detected out off another sample S receiving light L radiated by the second light radiation section 21 while flowing through the flow channel 2, it is desirable to control the flow rate of the samples S as described before. By integrating the second light detection section 22 with the first light detection section 12 to form a single light detector in this way, the single light detector can contribute to the downsizing of the optical measurement apparatus 1.

(1-8): Second Opto-Electrical Conversion Section 23

The second opto-electrical conversion section 23 is a section for converting the optical information detected by the second light detection section 22 into an electrical signal.

If an option not to operate the second light radiation section 21 and the second light detection section 22 is selected on the basis of the results produced in the measurement processes carried out by the first sections 12, 13 and 14, control can also be executed so as not to operate the second opto-electrical conversion section 23.

The second opto-electrical conversion section 23 can be provided as a section separated from the first opto-electrical conversion section 13 or provided on the same electrical board 8 as the first opto-electrical conversion section 13 as shown in FIG. 4. As shown in FIG. 4, the first opto-electrical conversion section 13 is provided to function on the same electrical board 8 as the second opto-electrical conversion section 23. With the second opto-electrical conversion section 23 provided on the same electrical board 8 as the first opto-electrical conversion section 13, the first opto-electrical conversion section 13 and the second opto-electrical conversion section 23 can contribute to the downsizing of the optical measurement apparatus 1. In addition, the first AD conversion section 14 described above, the amplification section 3 to be described below and the second AD conversion section 24 also to be described below can also be provided on the same electrical board 8 as the first opto-electrical conversion section 13 and the second opto-electrical conversion section 23.

(1-9): Amplification Section 3

The amplification section 3 is a section for amplifying the analog electrical signal output by the second opto-electrical conversion section 23 at a gain determined on the basis of the digital electrical signal which is output by the first AD conversion section 14. In FIG. 1, the analog electrical signal generated by the second opto-electrical conversion section 23 typically as a voltage pulse pointed to by an arrow→appended to the right side of the second opto-electrical conversion section 23 is amplified by the amplification section 3 into an analog electrical signal pointed to by an arrow→appended to the right side of the amplification section 3. Typically, the amplified analog electrical signal pointed to by an arrow→appended to the right side of the amplification section 3 is a voltage pulse as shown in FIG. 1.

In the existing optical measurement apparatus, in general, the type of samples S is predicted and the voltage pulse serving as the analog electrical signal is amplified at a gain according to the predicted type before being converted into a digital electrical signal. In the case of the optical measurement method according to an embodiment, however, the samples S are assumed to have sizes different from each other and/or types also different from each other. Unlike the optical measurement apparatus according to an embodiment, the existing optical measurement apparatus is not capable of keeping up with such samples S. Thus, by predicting the type of sample S flowing through the flow channel in advance as disclosed in Patent Document 1, it is impossible to generate analyzable data from samples S having sizes different from each other and/or types also different from each other. As a result, the samples S are just wasted in some cases.

In the case of the optical measurement apparatus 1 according to an embodiment, however, measured data of samples S flowing through the flow channel 2 has already been obtained by the first sections 11, 12, 13 and 14. Thus, the gain of the amplification section 3 can be set in accordance with a digital electrical signal output by the first AD conversion section 14 at a value which is optimum for the size and type of the samples S. That is to say, the amplification section 3 is capable of amplifying an analog electrical signal at a gain optimum for the size and type of the samples S. In addition, since the amplification section 3 is capable of amplifying an analog electrical signal at a gain optimum for the size and type of the samples S, there are very few cases in which the eventually obtained data cannot be analyzed. As a result, the number of wasted samples S can be reduced to a minimum.

It is to be noted that, if an option not to operate the second light radiation section 21, the second light detection section 22 and the second opto-electrical conversion section 23 is taken on the basis of results produced in measurement processes carried out by the first sections 12, 13 and 14, control can be executed to also put the amplification section 3 in an inoperative state.

The place at which the amplification section 3 is to be provided is not prescribed in particular. For example, the amplification section 3 can be provided on the same electrical board 8 as the first opto-electrical conversion section 13, the first AD conversion section 14, the second opto-electrical conversion section 23 and the second AD conversion section 24 which have been described earlier as shown in FIG. 4.

(1-10): Second AD Conversion Section 24

The second AD conversion section 24 is a section for converting the amplified analog electrical signal output by the amplification section 3 into a digital electrical signal in an AD conversion process.

In the optical measurement apparatus 1 according to an embodiment, the amplification section 3 amplifies the analog electrical signal output by the second opto-electrical conversion section 23 at an optimum gain as described earlier. Thus, by converting the amplified analog electrical signal output by the amplification section 3 into a digital electrical signal in an AD conversion process carried out by the second AD conversion section 24, detailed data can be obtained with a high degree of accuracy.

The second AD conversion section 24 can be provided as a section separated from the first AD conversion section 14 or on the same electrical board 8 as the first AD conversion section 14 as shown in FIG. 4. As shown in this figure, the first AD conversion section 14 is provided to function on the same electrical board 8 as the second AD conversion section 24. With the second AD conversion section 24 provided on the same electrical board 8 as the first AD conversion section 14, the first AD conversion section 14 and the second AD conversion section 24 can contribute to the downsizing of the optical measurement apparatus 1.

(1-11): Flow-Rate Measurement Section 4

The flow-rate measurement section 4 is a section for measuring the flow rate of samples S which are flowing through the flow channel 2. In the present application, the flow-rate measurement section 4 is not an absolutely required section, but an optional one. By providing the flow-rate measurement section 4, however, the timings of the light radiations from the first light radiation section 11 and the second light radiation section 21 which have been described before can be controlled in accordance with a flow rate of the samples S.

Figure 5:
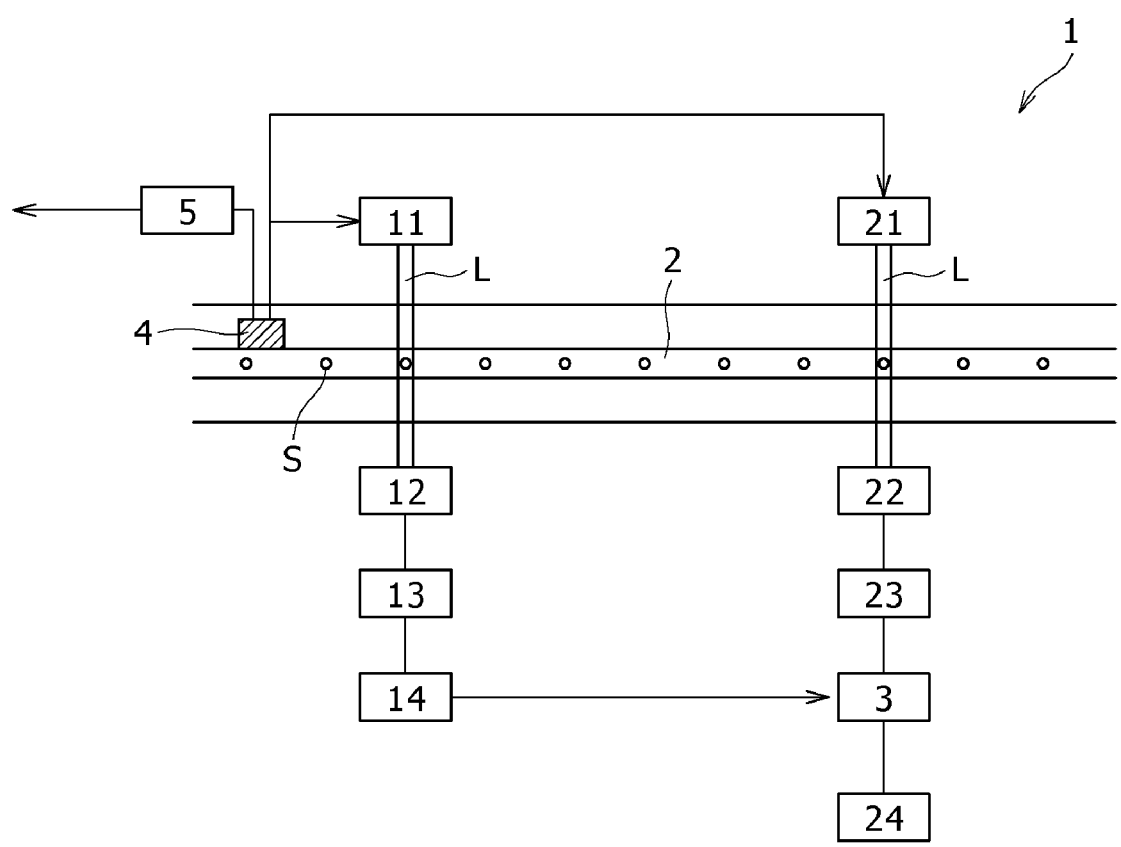
FIG. 5 is a conceptual diagram showing a model of an optical measurement apparatus according to a still further embodiment which is different from the embodiments shown in FIGS. 1, 2 and 4.

The place at which the flow-rate measurement section 4 is to be provided is not prescribed in particular. That is to say, the flow-rate measurement section 4 can be provided at any location as long as, at the location, the flow-rate measurement section 4 can be used for measuring the flow rate of the samples S. In addition, the location to install the flow-rate measurement section 4 can be determined and designed with a high degree of freedom. For example, the flow-rate measurement section 4 can be provided at a location relatively on the upstream side of the flow channel 2 as shown in FIG. 5.

In addition, the number of locations for installing flow-rate measurement sections 4 is also not prescribed in particular either. That is to say, two or more flow-rate measurement sections 4 can also be provided in order to measure a difference between flow rates on the upstream and downstream sides of the flow channel 2 and to measure the flow rate with a higher degree of accuracy.

It is to be noted that the type of the flow-rate measurement section 4 usable in the optical measurement apparatus 1 according to an embodiment is also not prescribed in particular either. That is to say, the flow-rate measurement section 4 can have any type as long as the flow-rate measurement section 4 can be used for measuring the flow rate of the samples S. For example, the flow-rate measurement section 4 can be selected as a section to be used in the optical measurement apparatus 1 with a high degree of freedom from commonly known flow-rate meters.

(1-12): Flow-Rate Control Section 5

The flow-rate control section 5 is a section for controlling the flow rate of samples S which are flowing through the flow channel 2. In the present application, the flow-rate control section 5 is not an absolutely required section, but an optional one. By providing the flow-rate control section 5, however, the flow rate of the samples S can be adjusted to match the timings of the light radiations from the first light radiation section 11 and the second light radiation section 21 which have been described before. If the flow rate of the samples S can be adjusted to match the timings of the light radiations from the first light radiation section 11 and the second light radiation section 21, various kinds of data can be obtained from the samples S with a higher degree of reliability. Thus, the precision of the measurement processes can be improved.

In addition, the flow rate of the samples S can be controlled also in order to prevent optical information from being detected out off a sample S receiving light L radiated by the first light radiation section 11 while flowing through the flow channel 2 at the same time as optical information detected out off another sample S receiving light L radiated by the second light radiation section 21 while flowing through the flow channel 2 as described before. By controlling the flow rate of the samples S in this way, the first light detection section 12 and the second light detection section 22 can be integrated with each other to form a single light detector. By virtue of such a single light detector, the size of the optical measurement apparatus 1 can be reduced.

The place at which the flow-rate control section 5 is to be provided is not prescribed in particular. That is to say, the flow-rate control section 5 can be provided at any location as long as, at the location, the flow-rate control section 5 can be used for controlling the flow rate of the samples S. In addition, the location to install the flow-rate control section 5 can be determined and designed with a high degree of freedom. For example, the flow-rate control section 5 can be provided on the same electric board as the first opto-electrical conversion section 13, the first AD conversion section 14, the second opto-electrical conversion section 23, the amplification section 3 and the second AD conversion section 24 which have been described earlier in a configuration shown in none of the figures.

The control method to be adopted by the flow-rate control section 5 is also not prescribed in particular either. That is to say, any control method can be selected for the flow-rate control section 5 with a high degree of freedom as long as the method can be used for controlling the flow rate of the samples S which are flowing through the flow channel 2. For example, in accordance with a typical control method carried out in a configuration shown in none of the figures, the flow rate of a sheath flow F102 to the flow channel 2 and the flow rate of the sample flow F101 to the flow channel 2 are adjusted to match the timings of the light radiations from the first light radiation section 11 and the second light radiation section 21 which have been described earlier. For the sheath flow F102 also mentioned in descriptions given below, the reader is suggested to refer to FIG. 7.

(1-13): Temperature Control Section 6

The temperature control section 6 is a section for controlling the temperature inside the flow channel 2. As described earlier, in accordance with the present application, the measurement processes are carried out at different locations in the flow channel 2. Thus, if the temperature in the flow channel 2 varies undesirably from location to location, the measurement processes cannot be carried out with a high degree of accuracy. It is thus desirable to provide the temperature control section 6 in the optical measurement apparatus 1 according to an embodiment.

Figure 6:
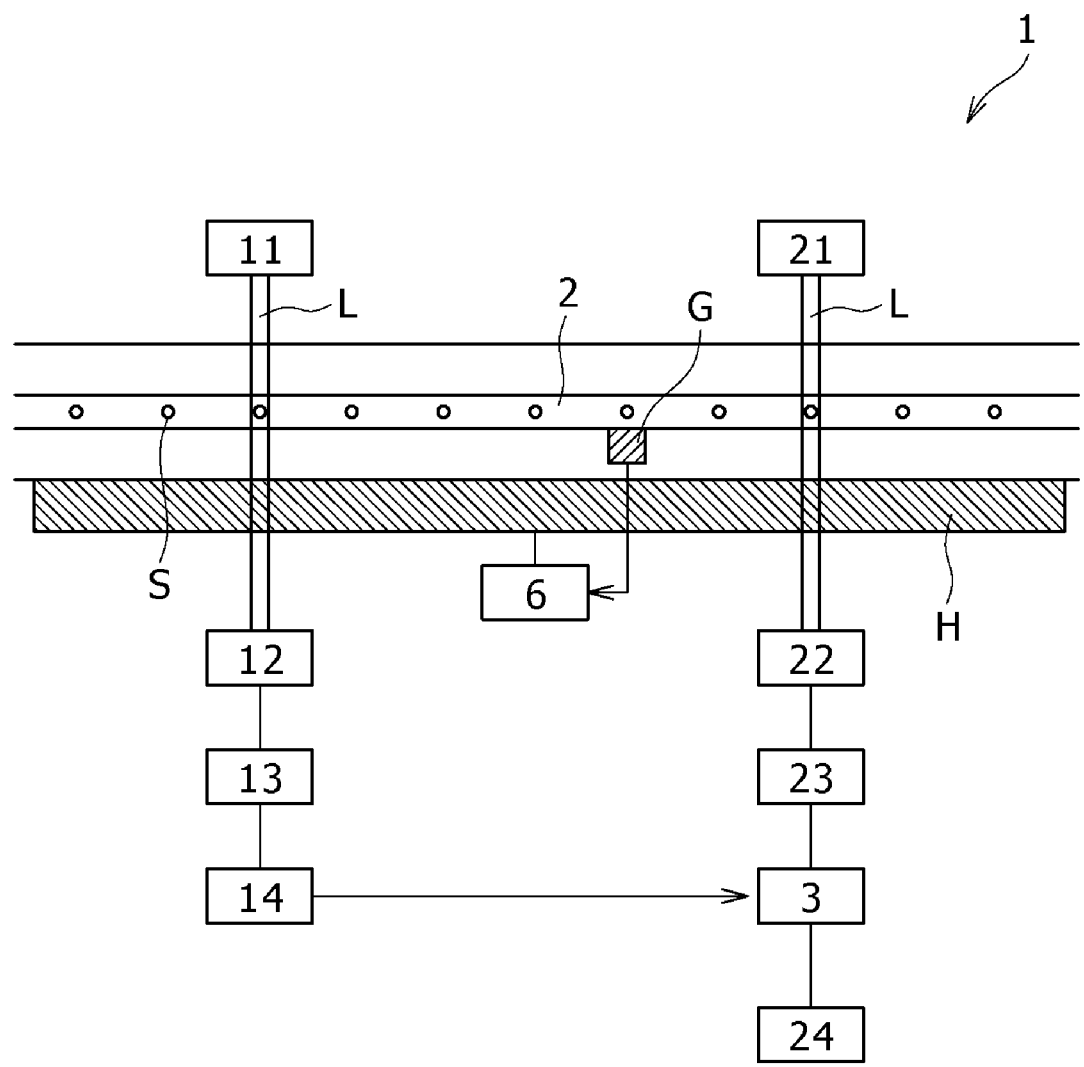
FIG. 6 is a conceptual diagram showing a model of an optical measurement apparatus according to a still further embodiment which is different from the embodiments shown in FIGS. 1, 2, 4 and 5.

The control method to be adopted by the temperature control section 6 is not prescribed in particular. That is to say, any control method can be selected for the temperature control section 6 with a high degree of freedom as long as the method can be used for controlling the temperature in the flow channel 2. For example, the temperature control section 6 employing a heater and a temperature controller H is provided on a board whereas a temperature sensor G is installed on the flow channel 2. The heater typically has patterned electrodes whereas the temperature controller H makes use of typically a Peltier device for controlling the heater. The temperature detected by the temperature sensor G is fed back to the temperature control section 6 in order to control the temperature in the flow channel 2. For the heater and the temperature sensor G, the reader is suggested to refer to FIG. 6.

2: Flow Site Meter

Figure 7:
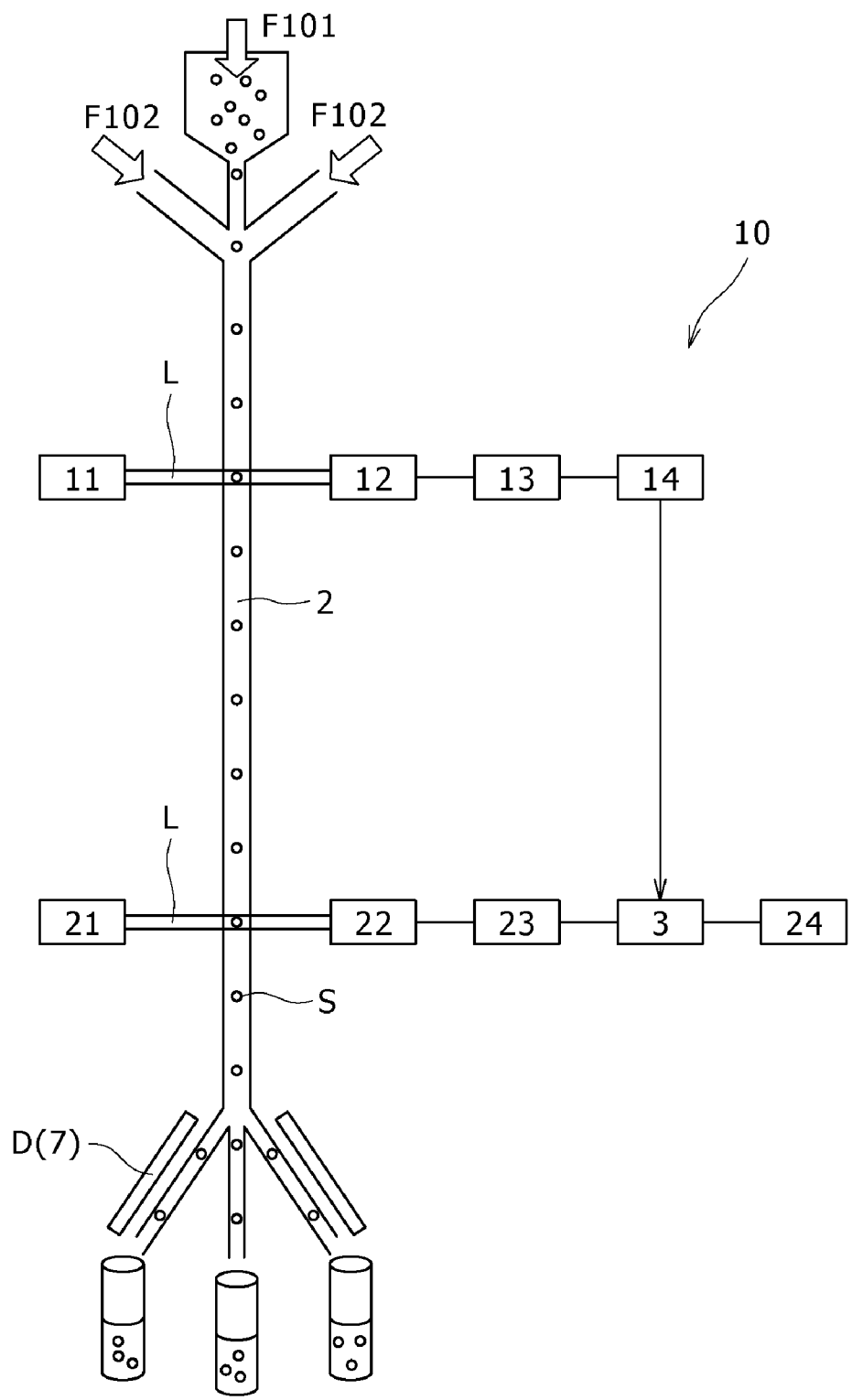
FIG. 7 is a conceptual diagram showing a model of a flow site meter according to an embodiment.

Taking advantage of the high precision of the optical measurement apparatus 1 according to an embodiment, inventors of the present application apply the optical measurement apparatus 1 to a flow site meter. FIG. 7 is a conceptual diagram showing a model of a flow site meter 10 according to an embodiment.

As shown in the figure, the flow site meter 10 provided by the present application employs at least a flow channel 2, a first light radiation section 11, a first light detection section 12, a first opto-electrical conversion section 13, a first AD conversion section 14, a second light radiation section 21, a second light detection section 22, a second opto-electrical conversion section 23, an amplification section 3, a second AD conversion section 24 and a sorting section 7. It is to be noted that the flow channel 2, the first light radiation section 11, the first light detection section 12, the first opto-electrical conversion section 13, the first AD conversion section 14, the second light radiation section 21, the second light detection section 22, the second opto-electrical conversion section 23, the amplification section 3 and the second AD conversion section 24 are identical with those employed in the optical measurement apparatus 1 and not described again in this chapter in order to avoid duplications of explanations.

(2-1): Sorting Section 7

The sorting section 7 is a section for sorting the samples S on the basis of the digital electrical signal obtained as a result of the analog-to-digital process carried out by the second AD conversion section 24. Typically, the digital electrical signal obtained as a result of the analog-to-digital process carried out by the second AD conversion section 24 represents the attributes of every sample S. For example, the attributes of a sample include the size, state and internal structure of the sample S. Thus, the sorting section 7 typically makes use of a deflection plate D or the like on the downstream side of the flow channel 2 to serve as a plate for sorting the samples S on the basis of the size, state and internal structure of every sample S.

In the typical configuration shown in FIG. 7, the flow site meter 10 employs a branch flow channel on the downstream side of the flow channel 2. It is to be noted, however, that the scope of the present application is by no means limited to this typical configuration. For example, in a configuration shown in none of the figures, on the downstream side of the flow channel 2, ultrasonic sound waves are used for generating liquid droplets including samples S and electric charge is added to each of the droplets. Then, the deflection plate D or the like is used for sorting the samples S.

3: Optical Measurement Method

Figure 8:
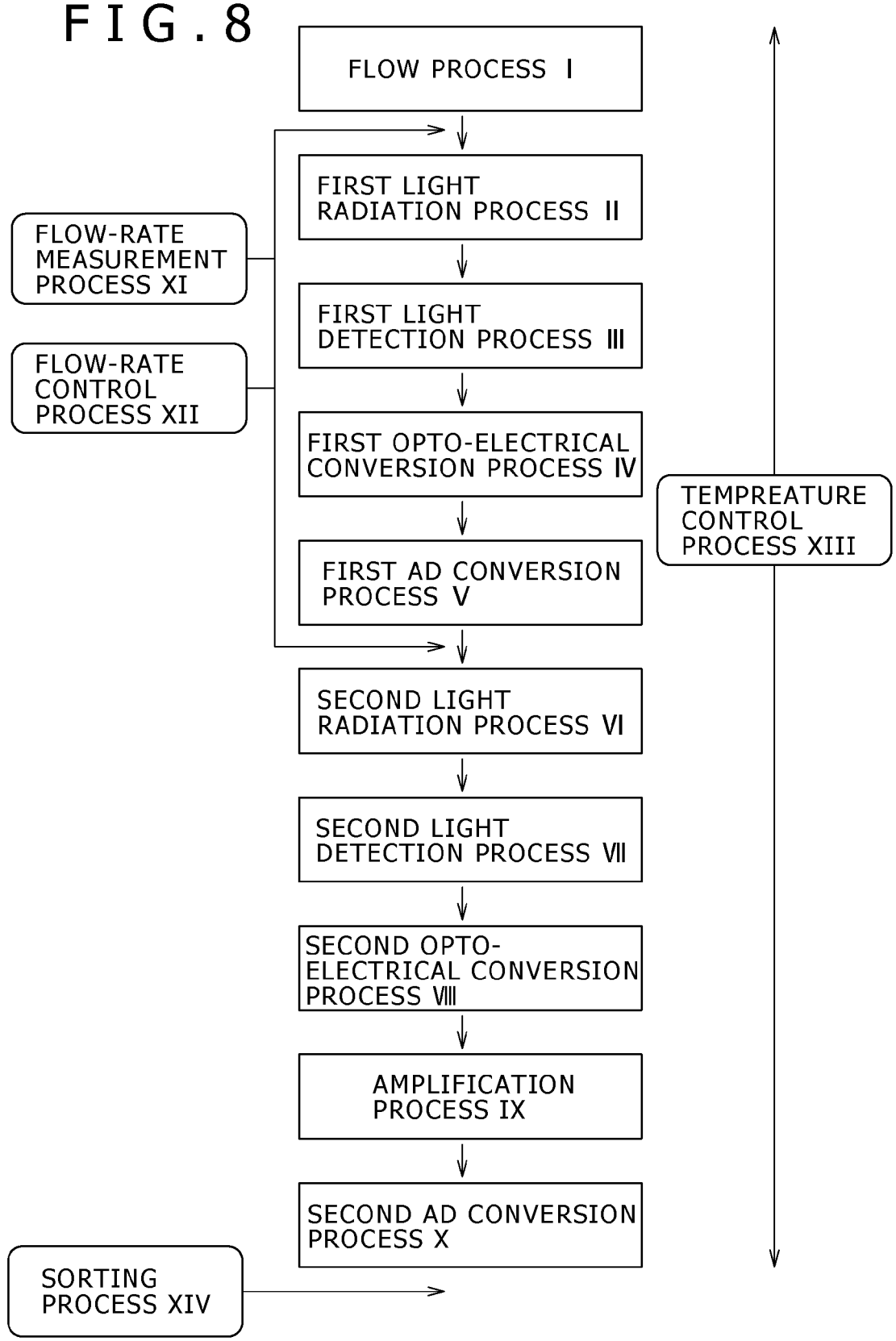
FIG. 8 shows a flowchart representing an optical measurement method provided by the present application.

FIG. 8 shows a flowchart representing an optical measurement method 100 provided by the present application.

The optical measurement method 100 provided by the present application is executed to carry out at least main processes such as a flow process I, a first light radiation process II, a first light detection process III, a first opto-electrical conversion process IV, a first AD conversion process V, a second light radiation process VI, a second light detection process VII, a second opto-electrical conversion process VIII, an amplification process IX and a second AD conversion process X. In addition, if necessary, the optical measurement method 100 provided by the present application is executed to carry out a flow-rate measurement process XI, a flow-rate control process XII, a temperature control process XIII and a sorting process XIV.

(3-1): Flow Process I

The flow process is a process of driving samples S to flow through the flow channel 2.

The method of driving samples S to flow through the flow channel 2 is not prescribed in particular. For example, it is possible to adopt a method for driving samples S to flow through the flow channel 2 to serve as a method by which, while a sample flow F101 including samples S is being merged with two sheath flows F102 coming from sources on both sides of the flow channel 2, the two sheath flows F102 are used for the purpose of speeding up rectification of the flow for transporting the samples S. Typically, each of the two sheath flows F102 is a flow of liquid media. By transporting the samples S in this way, it is possible to create a laminated flow of the flow F101 which includes samples S. Thus, a better flow of the samples S is possible. If the liquid-media flows each serving as a sheath flow F102 is used as a flow provided with a function of speeding up rectification of the flow for transporting the samples S, the type of the liquid-media flow is also not prescribed in particular either. However, if the sample S is a cell for example, an isotonic sodium chloride solution can be used as the liquid media.

It is desirable to modify in advance the samples S by a fluorescently labeled material such as a fluorescent substance (such as a fluorescent pigment), a radioactive substance, an intercalater or microbeads so that, in the first light detection process III and the second light detection process VII which will be described later, optical information can be detected from the samples S. If the fluorescent pigment is used, the type of the fluorescent pigment is also not prescribed in particular either. That is to say, the fluorescent pigment can be selected from commonly known fluorescent pigments. As an alternative, the fluorescent pigment can be a combination of two or more pigments which are selected from the commonly known fluorescent pigments. Typical examples of the commonly known fluorescent pigments are Cascade Blue, Pacific Blue, the FITC (Fluorescein isothiocyanate), the PE (Phycoerythrin), the PI (Propidium Iodide), the TR (Texas Red), the PerCP (Peridinin Chlorophyll Protein), the APC (Allophycocyanin), the DAPI (4',6-Diamidino-2-phenylindole), Cy3, Cy5 and Cy7.

If the sample S itself emits light as is the case with the fluorescent protein, it is not necessary to modify the sample S by a fluorescently labeled material. In addition, if the samples S are materials capable of changing their fluorescent pigment due to progress of interactions among the materials inside the flow channel 2 as is the case with the FRET principle, it is also unnecessary to modify the sample S by a fluorescently labeled material.

(3-2): First Light Radiation Process II

The first light radiation process II is a process carried out by the first light radiation section 11 to radiate light L to samples S which are flowing through the flow channel 2.

The type of light L radiated in the first light radiation process II is not prescribed in particular. It is desirable, however, to radiate light L having a constant direction, a constant wavelength and a constant intensity in order to obtain fluorescent or scattered light, which is generated by the samples S, with a high degree of reliability. For example, the light L radiated by the first light radiation section 11 in the execution of the first light radiation process II is laser light or light emitted by an LED (Light Emitting Device). If laser light is radiated in the execution of the first light radiation process II, the type of the laser light is also not prescribed in particular either. That is to say, the type of the laser can be any laser type or a combination of laser types. Typical examples of the laser type are an Ar (argon ion) laser, an He—Ne (helium-neon) laser, a dye laser and a Kr (Krypton) laser.

(3-3): First Light Detection Process III

The first light detection process III is a process carried out by the first light detection section 12 to detect optical information which is generated by the samples S due to radiation of light L from the first light radiation section 11 to the samples S in the first light radiation process II.

The light detection method adopted by the first light detection section 12 in the execution of the first light detection process III is not prescribed in particular. That is to say, the light detection method in the execution of the first light detection process III can be any light detection method as far as the method can be used for detecting the optical information generated by the samples S. In other words, the light detection method in the execution of the first light detection process III can be selected among commonly known light detection methods with a high degree of freedom. As an alternative, the light detection method in the execution of the first light detection process III can be created by combining two or more commonly known light detection methods with a high degree of freedom. Typical examples of the commonly known light detection methods are a fluorescent-light measurement method, a scattered-light measurement method, a transmitted-light measurement method, a reflected-light measurement method, a diffracted-light measurement method, an ultraviolet-light spectral measurement method, an infrared-light spectral measurement method, a Raman spectral measurement method, a FRET measurement method, a FISH measurement method, a variety of other spectrum measurement methods and the so-called multi-channel light detection method which is capable of detecting a plurality of pigments.

(3-4): First Opto-Electrical Conversion Process IV

The first opto-electrical conversion process IV is an opto-electrical conversion process carried out by the first opto-electrical conversion section 13 to convert the optical information detected by the first light detection section 12 in the first light detection process III into an analog electrical signal. The analog electrical signal generated in the execution of the first opto-electrical conversion process IV is typically a voltage pulse. In FIG. 1, the voltage pulse is pointed to by an arrow→which is appended to the right side of the first opto-electrical conversion section 13.

(3-5): First AD Conversion Process V

The first AD (analog-to-digital) conversion process V is an AD conversion process carried out by the first AD conversion section 14 to convert an analog electrical signal output by the first opto-electrical conversion section 13 in the first opto-electrical conversion process IV into a digital electrical signal.

In accordance with the existing optical measurement method, the AD conversion process to convert a voltage pulse serving as an analog electrical signal into a digital electrical signal is normally carried out after amplifying the analog electrical signal at a gain which is determined in advance. In the first AD conversion process V according to an embodiment, however, it is not necessary to set the gain in advance. That is to say, the first AD conversion section 14 carries out the first AD conversion process V after amplifying the analog electrical signal at any arbitrary gain. It is needless to say that the first AD conversion section 14 may also carry out the first AD conversion process V without amplifying the analog electrical signal.

The digital electrical signal obtained as a result of the first AD conversion process V is used for determining the gain of the amplification process IX as will be described later.

(3-6): Second Light Radiation Process VI

The second light radiation process VI is a light radiation process carried out by the second light radiation section 21 at a location on the downstream side of the flow channel 2. The second light radiation process VI is also a process of radiating light L to the samples S. That is to say, the second light radiation process VI is carried out to again radiate light L to the same samples S to which light has been radiated in the first light radiation process II. In most of the existing optical measurement methods each making use of a flow channel, the optical measurement of samples S flowing through the flow channel is generally carried out only once. In the case of the optical measurement method according to an embodiment, however, the optical measurement of the samples S can be carried out as many times as demanded provided that the samples S are flowing through the flow channel 2. Thus, in the optical measurement method according to an embodiment, the second light radiation section 21 is provided to serve as a section for carrying out the second light radiation process VI of re-radiating light to the samples S after radiation of light by the first light radiation section 11 to the samples S while the samples S are flowing through the flow channel 2.

It addition, in accordance with results produced in a variety of measurement processes carried out in the first processes III, IV and V, it is free to select an option not to carry out the second light radiation process VI. For example, if the results produced in a variety of measurement processes carried out by in the first processes III, IV and V are already ideal data, there is a conceivable case in which it is not necessary to carry out measurement processes with a high degree of precision by driving the second light radiation section 21, the second light detection section 22, the second opto-electrical conversion section 23, the amplification section 3 and the second AD conversion section 24 to carry out the second light radiation process VI, the second light detection process VII, the second opto-electrical conversion process VIII, the amplification process IX and the second AD conversion process X respectively.

In a case in which two or more samples S are flowing continuously or in similar cases, even if the second processes VI, VII, VIII, IX and X are carried out, it is not possible to obtain data which can be used for analyzing the samples S.

FIG. 3 is a diagram showing graphs representing a pulse signal of two contiguous samples S flowing in the form of a doublet and a pulse signal of three contiguous samples S flowing in the form of a triplet. Each of the pulse signal of the two contiguous samples S flowing in the form represented by the doublet graph shown in FIG. 3 and the pulse signal of the three contiguous samples S flowing in the form represented by the triplet graph shown in FIG. 3 undesirably has a plurality of peaks so that the samples S cannot be analyzed. If such results are eventually produced in measurement processes carried out by the first sections 12, 13 and 14, control can be executed to select an option not to drive the second light radiation section 21 to carry out the second light radiation process VI. Thus, wasteful measurement processes can be eliminated. As a result, necessary measurement processes can be carried out with a high degree of efficiency. In addition, since unanalyzable data can be omitted in advance, it is possible to simplify an algorithm which is required for analyzing data obtained as a result of the necessary measurement processes.

By the same token, the type of the light L radiated in the execution of the second light radiation process VI is also not prescribed in particular either. It is desirable, however, to radiate light L having a constant direction, a constant wavelength and a constant intensity in order to obtain fluorescent or scattered light, which is generated by the samples S, with a high degree of reliability. For example, the light L radiated by the second light radiation section 21 in the execution of the second light radiation process VI is laser light or light emitted by an LED (Light Emitting Device). If laser light is radiated by the second light radiation section 21 in the execution of the second light radiation process VI as the light L, the type of the laser light is also not prescribed in particular either. That is to say, the type of the laser can be any laser type or a combination of laser types. Typical examples of the laser type are an Ar (argon ion) laser, an He—Ne (helium-neon) laser, a dye laser and a Kr (Krypton) laser.

(3-7): Second Light Detection Process VII

The second light detection process VII is a process carried out by the second light detection section 22 to detect optical information which is generated by the samples S due to radiation of light from the second light radiation section 21 to the samples S in the execution of the second light radiation process VI. In the optical measurement apparatus 1 according to an embodiment, the second light detection section 22 serves as a section for again detecting optical information generated by the samples S, optical information generated by which has already been detected in the execution of the first light detection process III, while the samples S are flowing through the flow channel 2 in the execution of the second light detection process VII.

It is to be noted that, if the second light radiation process VI is not carried out in accordance with an option selected on the basis of the results produced in the first processes III, IV and V, control can also be executed so as not to execute the second light detection process VII.

The type of a light detection method for carrying out the second light detection process VII is not prescribed in particular. That is to say, the type of the light detection method can be any type as far as the light detection method can be adopted for detecting the optical information generated by the samples S. In other words, the second light detection section 22 can be selected among commonly known light detectors with a high degree of freedom. As an alternative, the second light detection section 22 can be constructed by combining two or more commonly known light detectors with different types with a high degree of freedom. Typical examples of the commonly known light detectors are a fluorescent-light measurement device, a scattered-light measurement device, a transmitted-light measurement device, a reflected-light measurement device, a diffracted-light measurement device, an ultraviolet-light spectral measurement device, an infrared-light spectral measurement device, a Raman spectral measurement device, a FRET measurement device, a FISH measurement device, other spectroscopes of a variety of types and the so-called multi-channel light detector which is an array of a plurality of light detectors.

(3-8): Second Opto-Electrical Conversion Process VIII

The second opto-electrical conversion process VIII is a process carried out by the second opto-electrical conversion section 23 to convert the optical information detected by the second light detection section 22 in the second light detection process VII into an electrical signal.

If the second light radiation process VI and the second light detection process VII are not carried out in accordance with an option selected on the basis of the results produced in the first processes III, IV and V, control can also be executed so as not to drive the second opto-electrical conversion section 23 to perform the second opto-electrical conversion process VIII.

(3-9): Amplification Process IX

The amplification process IX is a process carried out by the amplification section 3 to amplify the analog electrical signal output by the second opto-electrical conversion section 23 in the second opto-electrical conversion process VIII at a gain based on the digital electrical signal output by the first AD conversion section 14 as a result of the first AD conversion process V in FIG. 1, the analog electrical signal generated by the second opto-electrical conversion section 23 typically as a voltage pulse pointed to by an arrow→appended to the right side of the second opto-electrical conversion section 23 is amplified by the amplification section 3 into an analog electrical signal pointed to by an arrow→appended to the right side of the amplification section 3. Typically, the amplified analog electrical signal pointed to by an arrow→appended to the right side of the amplification section 3 is a voltage pulse as shown in FIG. 1.

In the existing optical measurement apparatus, in general, the type of samples S is predicted and the voltage pulse serving as the analog electrical signal is amplified at a gain according to the predicted type before being converted into a digital electrical signal. In the case of the optical measurement method according to an embodiment, however, the samples S are assumed to have sizes different from each other and/or types also different from each other. Unlike the optical measurement apparatus according to an embodiment, the existing optical measurement apparatus is not capable of keeping up with such samples S. Thus, by predicting the type of sample S flowing through the flow channel in advance as disclosed in Patent Document 1, it is impossible to generate analyzable data from samples S having sizes different from each other and/or types also different from each other. As a result, the samples S are just wasted in some cases.

In the case of the optical measurement apparatus 1 according to an embodiment, however, measured data of samples S flowing through the flow channel 2 has already been obtained by the first light sections 11, 12, 13 and 14. Thus, the gain of the amplification section 3 can be set in accordance with a digital electrical signal output by the first AD conversion section 14 at a value which is optimum for the size and type of the samples S. That is to say, the amplification section 3 is capable of amplifying an analog electrical signal at a gain optimum for the size and type of the samples S. In addition, since the amplification section 3 is capable of amplifying an analog electrical signal at a gain optimum for the size and type of the samples S, there are very few cases in which the eventually obtained data cannot be analyzed. As a result, the number of wasted samples S can be reduced to a minimum.

It is to be noted that, if the second light radiation process VI, the second light detection process VII and the second opto-electrical conversion process VIII are not carried out in accordance with an option selected on the basis of results measured by the first sections 11, 12, 13 and 14, control can be executed to also put the amplification section 3 in an inoperative state in which the amplification process IX is not carried out.

(3-10): Second AD Conversion Process X

The second AD conversion process X is a process carried out by the second AD conversion section 24 to convert the amplified analog electrical signal output by the amplification section 3 in the execution of the amplification process IX into a digital electrical signal.

In accordance with the optical measurement method according to an embodiment, the amplification section 3 amplifies the analog electrical signal, which has been output in the execution of the second opto-electrical conversion process VIII, at an optimum gain in the execution of the amplification process IX as described earlier. Thus, by converting the amplified analog electrical signal into a digital electrical signal, detailed data can be obtained with a high degree of accuracy.

(3-11): Flow-Rate Measurement Process XI

The flow-rate measurement process XI is a process carried out by the flow-rate measurement section 4 to measure the flow rate of samples S which are flowing through the flow channel 2. In the present application, the flow-rate measurement process XI is not an absolutely required process, but an optional one. By providing the optical measurement apparatus 1 with the flow-rate measurement section 4, however, the timings of the light radiations in the first light radiation process II and the second light radiation process VI can be controlled in accordance with the measured flow rate of the samples S.

The number of times the flow-rate measurement process XI is to be carried out and timings to perform the flow-rate measurement process XI are not prescribed in particular. That is to say, the flow-rate measurement process XI can be carried out with any timings as many times as necessary with a high degree of freedom as long as the flow-rate measurement process XI is performed after the execution of the flow process I. In the case of the present application, as shown in FIG. 8, it is desirable to carry out the flow-rate measurement process XI particularly prior to the first light radiation process II and prior to the second light radiation process VI. This is because the flow rate measured in the flow-rate measurement process XI carried out prior to the first light radiation process II as the flow rate of the samples S can be used for controlling the timing of the light radiation in the first light radiation process II. By the same token, the flow rate measured in the flow-rate measurement process XI carried out prior to the second light radiation process VI as the flow rate of the samples S can be used for controlling the timing of the light radiation in the second light radiation process VI.

It is to be noted that the flow-rate measurement method adopted by the flow-rate measurement section 4 to carry out the flow-rate measurement process XI is not prescribed in particular. That is to say, the flow-rate measurement section 4 is allowed to adopt any flow-rate measurement method as long as the method can be used for measuring the flow rate of the samples S. For example, a flow-rate measurement method making use of a commonly known flow rate meter or the like can be typically selected with a high degree of freedom.

(3-12): Flow-Rate Control Process XII

The flow-rate control process XII is a process carried out by the flow-rate control section 5 to control the flow rate of samples S which are flowing through the flow channel 2. In the present application, the flow-rate control process XII is not an absolutely required process, but an optional one. By providing the optical measurement apparatus 1 with the flow-rate control section 5, however, the flow rate of the samples S can be adjusted to match the timings of the light radiations in the first light radiation process II and the second light radiation process VI. If the flow rate of the samples S can be adjusted to match the timings of the light radiations in the first light radiation process II and the second light radiation process VI, various kinds of data can be obtained from the samples S with a higher degree of reliability. Thus, the precision of the measurement processes can be improved.

In addition, the flow rate of the samples S can be controlled also in order to prevent optical information from being detected out off a sample S receiving light L radiated by the first light radiation section 11 while flowing through the flow channel 2 at the same time as optical information detected out off another sample S receiving light L radiated by the second light radiation section 21 while flowing through the flow channel 2 as described before. By controlling the flow rate of the samples S in this way, the first light detection section 12 and the second light detection section 22 can be integrated with each other to form a single light detector. Thus, the size of the optical measurement apparatus 1 can be reduced.

The number of times the flow-rate control process XII is to be carried out and timings to perform the flow-rate control process XII are not prescribed in particular. That is to say, the flow-rate control process XII can be carried out with any timings as many times as necessary with a high degree of freedom as long as the flow-rate control process XII is performed after the execution of the flow process I. In the case of the present application, as shown in FIG. 8, it is desirable to carry out the flow-rate control process XII particularly prior to the first light radiation process II and prior to the second light radiation process VI. This is because, by carrying out the flow-rate control process XII prior to the first light radiation process II, it is possible to control the flow rate of the samples S with a timing adjusted to the timing of the light radiation of the first light radiation process II. By the same token, by carrying out the flow-rate control process XII prior to the second light radiation process VI, it is possible to control the flow rate of the samples S with a timing adjusted to the timing of the light radiation of the second light radiation process VI.

The control method to be adopted by the flow-rate control section 5 in carrying out the flow-rate control process XII is not prescribed in particular. That is to say, any control method can be selected for the flow-rate control section 5 with a high degree of freedom as long as the method can be used for controlling the flow rate of the samples S which are flowing through the flow channel 2. For example, according to a typical control method carried out in a configuration shown in none of the figures, the flow rate of a sheath flow F102 to the flow channel 2 and the flow rate of the sample flow F101 to the flow channel 2 are adjusted to match the timings of the light radiations in the first light radiation process II and the second light radiation process VI.

(3-13): Temperature Control Process XIII

The temperature control process XIII is a process carried out by the temperature control section 6 to control the temperature inside the flow channel 2. As described earlier, in accordance with the present application, the measurement processes are carried out at different locations in the flow channel 2. Thus, if the temperature in the flow channel 2 varies undesirably from location to location, the measurement processes cannot be carried out with a high degree of accuracy. It is thus desirable to carry out the temperature control process XIII in accordance with the optical control method according to an embodiment.

The number of times the temperature control process XIII is to be carried out and timings to perform the temperature control process XIII are not prescribed in particular. That is to say, the temperature control process XIII can be carried out with any timings as many times as necessary with a high degree of freedom as long as the temperature in the flow channel 2 can be controlled. In the case of the present application, as shown in FIG. 8, it is desirable to particularly control the temperature in the flow channel 2 all the time in order to keep the temperature of the samples S flowing through the flow channel 2 at a constant. In this way, the precision of the measurement processes can be improved.

The control method to be adopted by the temperature control section 6 in carrying out the temperature control process XIII is not prescribed in particular. That is to say, any control method can be selected for the temperature control section 6 with a high degree of freedom as long as the method can be used for controlling the temperature in the flow channel 2. For example, the temperature control section 6 employing a heater and a temperature controller H is provided on a board whereas a temperature sensor G is installed on the flow channel 2. The heater typically has patterned electrodes whereas the temperature controller H makes use of typically a Peltier device for controlling the heater. The temperature detected by the temperature sensor G is fed back to the temperature control section 6 in order to control the temperature in the flow channel 2. For the heater and the temperature sensor G, the reader is suggested to refer to the conceptual diagram of FIG. 6.

(3-14): Sorting Process XIV

The sorting process XIV is a process carried out by the sorting section 7 to sort the samples S on the basis of the digital electrical signal obtained as a result of the AD (analog-to-digital) process X carried out by the second AD conversion section 24. In the present application, the sorting process XIV is not an absolutely required process, but an optional one. By providing the optical measurement apparatus 1 with the sorting section 7 to serve as a section for carrying out the sorting process XIV, however, the optical control method according to an embodiment can be executed as a method of a flow-sitemetry process.

In accordance with a typical sorting method, the digital electrical signal obtained as a result of the analog-to-digital process X carried out by the second AD conversion section 24 represents the attributes of a sample S. Typically, the attributes of a sample include the size, state and internal structure of the sample S. Thus, the sorting section 7 makes use of a deflection plate D or the like on the downstream side of the flow channel 2 to serve as a plate for sorting the samples S on the basis of the size, state and internal structure of every sample S.

INDUSTRIAL APPLICABILITY

In the optical measurement apparatus 1 according to an embodiment, the amplification section 3 amplifies an analog electrical signal, which is generated as a result of processes carried out by the second sections 21, 22 and 23 as a signal for samples S, at an optimum gain determined on the basis of information produced earlier by the first sections 11, 12 and 13 as information on the same samples S. Then, the second AD conversion section 24 carries out an AD (analog-to-digital) process to convert the amplified analog electrical signal into a digital electrical signal. Thus, no samples S are wasted. As a result, it is possible to efficiently and reliably improve the precision of the digital electrical signal which results from the analog-to-digital process. Accordingly, by the technology according to an embodiment, it is possible to contribute to the improvements of the sample sorting and analyzing technology in a variety of fields such as the medical field, the pharmaceutical field, the clinical examination field, the food field, the agricultural field, the engineering field, the forensic pathological field and the criminal identification field. Particularly, in the case of the medical field, the technology according to an embodiment plays an important role in subfields such as pathology, tumor immunology, transplantations, genetics, regenerative medicine and chemotherapy.

It should be understood that various changes and modifications to the presently preferred embodiments described herein will be apparent to those skilled in the art. Such changes and modifications can be made without departing from the spirit and scope and without diminishing its intended advantages. It is therefore intended that such changes and modifications be covered by the appended claims.

The application is claimed as follows:

1. An optical measurement apparatus comprising at least:
   a flow channel through which samples flow;
   first light radiation means for radiating light to said samples flowing through said flow channel;
   first light detection means for detecting optical information emitted from said samples due to said light radiated by said first light radiation means to said samples;
   first opto-electrical conversion means for carrying out an opto-electrical conversion process of converting said optical information detected by said first light detection means into an analog electrical signal;
   first analog-to-digital conversion means for carrying out an analog-to-digital conversion process of converting said analog electrical signal, which is output by said first opto-electrical conversion means, into a digital electrical signal;
   second light radiation means provided on the downstream side of said flow channel with respect to said first light radiation means for serving as a light radiation means for radiate light to said samples;
   second light detection means for detecting optical information emitted from said samples due to said light radiated by said second light radiation means;
   second opto-electrical conversion means for carrying out an opto-electrical conversion process of converting said optical information detected by said second light detection means into an analog electrical signal;
   amplification means for amplifying said analog electrical signal, which is output by said second opto-electrical conversion means, on the basis of said digital electrical signal output by said first analog-to-digital conversion means as a result of said analog-to-digital conversion process; and
   second analog-to-digital conversion means for converting said analog electrical signal amplified by said amplification means into a digital electrical signal.

2. The optical measurement apparatus according to claim 1, said optical measurement apparatus further having flow-rate measurement means for measuring the flow rate of said samples which are flowing through said flow channel.

3. The optical measurement apparatus according to claim 1, said optical measurement apparatus further having flow-rate control means for controlling the flow rate of said samples which are flowing through said flow channel.

4. The optical measurement apparatus according to claim 1, said optical measurement apparatus further having temperature control means for controlling the temperature in said flow channel.

5. The optical measurement apparatus according to claim 1 wherein said first light radiation means also functions as said second light radiation means.

6. The optical measurement apparatus according to claim 1 wherein said first light detection means also functions as said second light detection means.

7. The optical measurement apparatus according to claim 1 wherein said first opto-electrical conversion means also functions as said second opto-electrical conversion means.

8. The optical measurement apparatus according to claim 1 wherein said first analog-to-digital conversion means also functions as said second analog-to-digital conversion means.

9. A flow site meter comprising at least:
   a flow channel through which samples flow;
   first light radiation means for radiating light to said samples flowing through said flow channel;
   first light detection means for detecting optical information emitted from said samples due to said light radiated by said first light radiation means;
   first opto-electrical conversion means for carrying out an opto-electrical conversion process of converting said optical information detected by said first light detection means into an analog electrical signal;
   first analog-to-digital conversion means for carrying out an analog-to-digital conversion process of converting said analog electrical signal, which is output by said first opto-electrical conversion means, into a digital electrical signal;
   second light radiation means provided on the downstream side of said flow channel with respect to said first light radiation means to serve as light radiation means for radiating light to said samples;
   second light detection means for detecting optical information emitted from said samples due to said light radiated by said second light radiation means;
   second opto-electrical conversion means for carrying out an opto-electrical conversion process of converting said optical information detected by said second light detection means into an analog electrical signal;
   amplification means for amplifying said analog electrical signal, which is output by said second opto-electrical conversion means, on the basis of said digital electrical signal output by said first analog-to-digital conversion means as a result of said analog-to-digital conversion process;
   second analog-to-digital conversion means for converting said analog electrical signal amplified by said amplification means into a digital electrical signal; and
   sorting means for sorting said samples on the basis of said digital electrical signal output by said second analog-to-digital conversion means.

10. An optical measurement method comprising at least:
driving samples to flow through a flow channel;
radiating light to said samples flowing through said flow channel;
detecting optical information emitted from said samples due to said light radiated at said first light radiation step;
carrying out an opto-electrical conversion process of converting said optical information detected at said first light detection step into an analog electrical signal;
carrying out an analog-to-digital conversion process of converting said analog electrical signal, which is output at said first opto-electrical conversion step, into a digital electrical signal;
radiating light to said samples flowing through said flow channel at a location on the downstream side of said flow channel with respect to a location, at which said first light radiation step is executed;
detecting optical information emitted from said samples due to said light radiated at said second light radiation step:
carrying out an opto-electrical conversion process of converting said optical information detected at said second light detection step into an analog electrical signal;
amplifying said analog electrical signal, which is output at said second opto-electrical conversion step, on the basis of said digital electrical signal output at said first analog-to-digital conversion step; and
converting said analog electrical signal amplified at said amplification step into a digital electrical signal.

* * * * *